(12) United States Patent
Slusher et al.

(10) Patent No.: US 8,771,975 B2
(45) Date of Patent: Jul. 8, 2014

(54) QUANTITATION OF GCP ACTIVITY IN BIOLOGICAL SAMPLES

(75) Inventors: Barbara S. Slusher, Kingsville, MD (US); Michael Polydefkis, Baltimore, MD (US); Camilo Rojas, Baltimore, MD (US); Marigo Stathis, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 13/977,966

(22) PCT Filed: Jan. 5, 2012

(86) PCT No.: PCT/US2012/020295
§ 371 (c)(1),
(2), (4) Date: Sep. 12, 2013

(87) PCT Pub. No.: WO2012/094472
PCT Pub. Date: Jul. 12, 2012

(65) Prior Publication Data
US 2013/0344525 A1  Dec. 26, 2013

Related U.S. Application Data

(60) Provisional application No. 61/429,878, filed on Jan. 5, 2011.

(51) Int. Cl.
*C12N 9/48* (2006.01)
*C12Q 1/34* (2006.01)

(52) U.S. Cl.
USPC ............................................ 435/18; 435/212

(58) Field of Classification Search
USPC .................................................. 435/18, 212
See application file for complete search history.

(56) References Cited

PUBLICATIONS

Thomas et al., Analytical Chemistry, 404, 94-96, 2010.*
Carell et al. "A Novel Procedure for the Synthesis of Libraries Containing Small Organic Molecules," Angew. Chem. Int. Ed. Engl. 33(2):2059 (1994).
Carell et al. "A Solution-Phase Screening Procedure for the Isolation of Active Compounds from a Library of Molecules," Angew. Chem. Int. Ed. Engl. 33(20):2061 (1994).
Cho et al. "An Unnatural Bioploymer," Science 261:1303 (Sep. 3, 1993).
Cull, et al. "Screening for receptor ligands using large libraries of peptides linked to the C terminus of the lac repressor," Proc Natl. Acad Sci USA 89:1865-1869 (Mar. 1992).
Cwirla et al. "Peptides on phage: A vast library of peptides for identifying ligands," Proc. Natl. Acad. Sci. USA 87:6378-6382 (Aug. 1990).
Devlin, et al. "Random Peptide Libraries: A souce of Specific Protein Binding Molecules," Science 249:404-406 (1990).
DeWitt et al. ""Diversomers": An approach to nonpeptide, nonoligomeric chemical diversity," Proc. Natl. Acad. Sci. USA; 90:6909-6913 (Aug. 1993).
Erb, et al. "Recursive deconvolution of combinatorial chemical libraries," Proc. Natl. Acad. Sci. USA; 91:11422-11426 (Nov. 1994).
Felici, Franco; "Selection of Antibody Ligands from a Large Library of Oligopeptides Expressed on a Multivalent Exposition Vector," J. Mol. Biol. 222:301-310 (1991).
Fodor, et al. "Miltiplexed biochemcial assays with biological chips," Nature; 364:555-556 (Aug. 5, 1993).
Gallop, et al. "Applications of Combinatorial Technologies to Drug Discovery. 1. Background and Peptide Combinatorial Libraries," J. Med. Chem.; 37(9):1233-1251 (Apr. 29, 1994).
Houghten, et al. "The use of synthetic peptide combinatorial libraries for the identification of bioactive peptides," Biotechniques; 13(3):412-421 (1992).
Lam, et al. "A new type of synthetic peptide library for identifying ligand-binding activity," Nature, 354:82-84 (Nov. 7, 1991).
Lam, Kit S. "Application of combinatorial library methods in cancer research and drug discovery," Anti-Cancer Drug Design; 12:145-167 (1997).
Rovenská, et al., "Tissue Expression and Enzymologic Characterization of Human Prostate Specific Membrane Antigen and Its Rat and Pig Orthologs," The Prostate; 68:171-182 (2008).
Scott, et al. "Searching for Peptide Ligands with an Epitope Library," Science; 249(4967):386-390 (Jul. 27, 1990).
Slusher, et al., "Rat Brain N-Acetylated α-Linked Acidic Dipeptidase Activity," J. Biol. Chem. 265(34):21297-21301 (Dec. 5, 1990).
Zuckermann, et al. "Discovery of Nanomolar Ligands for 7-Transmembrane G-Protein-Coupled Receptors from a Diverse N-(Substituted)glycine Peptoid Library," J. Med. Chem. 37:2678-85 (1994).

* cited by examiner

*Primary Examiner* — Maryam Monshipouri
(74) *Attorney, Agent, or Firm* — Foley Hoag LLP (57) ABSTRACT

Provided herein are methods for quantitating glutamate carboxypeptidase II activity in a biological sample, such as a skin biopsy sample, and for determining whether an agent is inhibiting GCP in a subject.

20 Claims, 5 Drawing Sheets

QUANTITATION OF GCP ACTIVITY IN BIOLOGICAL SAMPLES

RELATED APPLICATIONS

This application is a National Stage Application of PCT/US2012/020295, filed Jan. 5, 2012, which claims the benefit of U.S. Provisional Application No. 61/429,878, filed Jan. 5, 2011, the content of which is expressly incorporated by reference herein in its entirety.

BACKGROUND

Excess glutamate is neurotoxic and contributes to a number of degenerative diseases of the central and peripheral nervous system. One source of glutamate in these tissues is N-acetyl-aspartyl-glutamate (NAAG), a dipeptide found in the brain and peripheral nerves. NAAG hydrolysis is catalyzed by glutamate carboxylase enzymes, including glutamate carboxypeptidase II and glutamate carboxylase III. Herein, GCPII and GCPIII are collectively referred to as GCP.

GCP is a highly expressed enzyme found on the surface of a number of cell types, including astrocytes and non-myelinating Schwann cells Inhibition of GCP-catalyzed NAAG hydrolysis is a promising therapy for the treatment of a number of neurodegenerative diseases. Indeed, genetic and pharmacological inhibition of GCP is neuroprotective in a variety of cell and animal disease models, and several GCP inhibitors are being investigated as therapeutics for the treatment of peripheral neuropathy and neuropathic pain.

Clinical development of a therapeutic agent (e.g., a GCP inhibitor) often use pharmacodynamic (PD) marker assays to determine what doses of the agent are required to elicit a pharmacologic response. Previously, NAAG levels in cerebrospinal fluid was the most common PD marker for monitoring GCP inhibition. However, collection of cerebrospinal fluid requires considerable skill and it is uncomfortable for patients. Also, NAAG measurement requires complicated laboratory techniques, such as HPLC or LC-MS/MS, and NAAG levels are only an indirect indicator of GCP inhibition.

Direct quantification of GCP enzyme activity would provide a more straightforward and accurate measurement of GCP inhibition. However, direct GCP activity measurement was thought to be unfeasible for use in PD marker assays in the clinic because GCP was believed to be predominantly expressed in the nervous system, prostate, intestinal tract, and kidney, tissues that are not easily accessible for collection from patients (See, e.g., Slusher et al., *J. Biol. Chem.* 265: 21297-21301 (1990)). Previous attempts to quantify GCP activity in more accessible tissues, such as the skin, have been unsuccessful (See, e.g., Rovenska et al., *Prostate* 68:171-182 (2008)). Thus, there is a need for new methods for quantitating GCP activity in easily obtainable biological samples, such as skin biopsies.

SUMMARY

Provided herein are methods for quantitating GCP activity in a biological sample, including conveniently obtainable samples, such as skin samples. In some embodiments, the biological sample includes endogenous NAAG and the method includes the step of reducing the amount of the endogenous NAAG in the biological sample. In certain embodiments the method also includes the steps of contacting the biological sample with exogenous NAAG, and/or detecting the amount of an exogenous NAAG cleavage product (e.g., glutamate and/or N-acetyl-aspartate) in the biological sample. The amount of exogenous NAAG cleavage product detected will correlate with the amount of GCP in the biological sample. In some embodiments, the biological sample is a skin biopsy. In some embodiments the skin biopsy was collected from a subject to whom a GCP inhibitor had been administered.

Also provided herein are methods for determining whether an agent (or a particular dose of an agent) inhibits GCP in a subject. In some embodiments, the methods include the steps of administering the agent to the subject, obtaining a biological sample from the subject, reducing the amount of endogenous NAAG in the biological sample, contacting the biological sample with exogenous NAAG, and/or detecting the amount of an exogenous NAAG cleavage product in the biological sample. In some embodiments, the amount of exogenous NAAG cleavage product is compared to the amount of exogenous NAAG cleavage product in a control sample (e.g., a biological sample collected from the subject before administration of the inhibitor). In general, a lower amount of exogenous NAAG cleavage product in the biological sample compared to the amount of exogenous NAAG cleavage product in a control sample indicates that the agent administered to the patient is inhibiting GCP in the subject.

In certain embodiments the methods described herein include the step of reducing the amount of endogenous NAAG in a biological sample. In some embodiments, this includes the steps of, homogenizing the biological sample in a buffer to create a homogenate (e.g., by sonication), centrifuging the homogenate to create a sample pellet that contains the GCP and a supernatant that contains the endogenous NAAG, and removing the supernatant from the sample.

In some embodiments, the methods described herein include the step of contacting a biological sample with exogenous NAAG. In some embodiments the exogenous NAAG incorporates a detectable label (e.g., a radioactive, a fluorescent, an enzymatic, a colorimetric and/or a chemiluminescent label). In certain embodiments, the detectable label is incorporated into the exogenous NAAG such that the detectable label remains attached to the exogenous NAAG cleavage product (e.g., glutamate or NAA) following cleavage of NAAG by GCP. In some embodiments, the detectable label is detected as an indication of the presence of the exogenous NAAG cleavage product. In some embodiments, the detected exogenous NAAG cleavage product is separated from remaining uncleaved exogenous NAAG before it is detected (e.g., by strong cation exchange chromatography).

BRIEF DESCRIPTION OF THE DRAWINGS

FIG. 1 shows the dependence of GCP activity in human skin biopsy on time of incubation. Human skin biopsies were sonicated for 2 minutes in ice. The resulting mixture was centrifuged at 16000×g; precipitate from each preparation was used as GCP source in the activity assay. Incubations with [$^3$H] NAAG (70 nM) at 37° C. were carried out at 0.5, 1, 2, 3, 5, 7.5, 14, 18 and 24 h. Time points correspond to incubations carried out with biopsies obtained from different donors. Major plot illustrates the correspondence of enzyme activity ([$^3$H]-glutamate production in dpm) with time while linearity was observed. Inset illustrates GCP activity measured at times up to 24 hours.

DETAILED DESCRIPTION

General

Provided herein are methods for quantitating glutamate carboxypeptidase II and glutamate carboxylase III (collectively referred to as GCP) activity in a biological sample. In certain embodiments, the method includes the steps of reducing the amount of the endogenous NAAG in the biological sample, contacting the biological sample with exogenous NAAG, and detecting the amount of an exogenous NAAG cleavage product (e.g., glutamate and/or N-acetyl-aspartate) in the biological sample. In general, the amount of exogenous NAAG cleavage product detected will correlate with amount of active GCP enzyme in the sample. Such methods can be used, for example, to determine whether an agent (or a particular dose of an agent) inhibits GCP activity in a subject.

Current methods for measuring GCP activity involve cerebral-spinal fluid collection, which requires considerable skill and can be uncomfortable to patients, and use mass spectrometry, which requires a specialized laboratory and expensive instrumentation. Consequently, such methods are inconvenient, complicated and poorly suited for the clinical environment. Previous attempts at measuring GCP activity in biological samples that are more conveniently obtained from a patient, such as skin biopsy samples, have been unsuccessful.

The methods provided herein enable the quantitation of GCP activity in conveniently obtainable biological samples, such as skin biopsy samples. The methods described herein have numerous advantages over the prior NAAG bioassay, including the ability to use a wider variety of sample types (including skin biopsy samples), the ability to use less expensive and time consuming sample analyses, and the ability to directly quantitate GCP activity. Furthermore, since the methods described herein allow for the use skin biopsies, which are readily accessible and can be collected multiple times from a single subject, the methods facilitate the evaluation of GCP activity both before and after administration of a potential GCP inhibiting agent, and at various time points following administration. Thus, provided herein are simple and direct methods for the measurement of GCP activity from tissue samples that are easily assessable in human subjects. Such methods can be used to monitor the efficacy of a GCP inhibitor in a subject and allow GCP activity to be directly used as a PD marker in the clinical development of GCP inhibitors.

DEFINITIONS

As used herein, the term "administering" means providing a pharmaceutical agent (e.g. a GCP inhibitor) or composition to a subject, and includes, but is not limited to, administering by a medical professional and self-administering.

The term "agent" is used herein to denote a chemical compound, a small molecule, a mixture of chemical compounds, a biological macromolecule (such as a nucleic acid, an antibody, a protein or portion thereof), or an extract made from biological materials such as bacteria, plants, fungi, or animal cells or tissues. Agents may be known in the art or identified as having a particular activity (e.g. inhibition of GCP) by a screening assay.

The term "biological sample," "tissue sample," or simply "sample" each refers to a collection of cells obtained from a tissue of a subject. The source of the tissue sample may be solid tissue, as from a fresh, frozen and/or preserved organ, tissue sample, biopsy, or aspirate; blood or any blood constituents, serum, blood; bodily fluids such as cerebral spinal fluid, amniotic fluid, peritoneal fluid or interstitial fluid, urine, saliva, stool, tears; or cells from any time in gestation or development of the subject. In certain embodiments, the biological sample is a skin biopsy sample (e.g., a skin punch).

The term "control" includes any portion of an experimental system designed to demonstrate that the factor being tested is responsible for the observed effect, and is therefore useful to isolate and quantify the effect of one variable on a system. For example, in certain embodiments of the methods described herein, the level of GCP activity in a biological sample is compared to the level of GCP activity in a control sample. When the test biological sample (e.g., a skin biopsy) is obtained from a subject who has been administered an agent, the control sample can be a sample (e.g., a skin biopsy) obtained from the same subject before the subject was administered the agent. Alternatively, the control sample can be a sample obtained from a different subject who was not administered the agent. In certain embodiments, the GCP activity in the test biological sample is compared to the mean or median GCP activity of a plurality of control samples.

As used herein, the term "endogenous NAAG" refers to N-acetyl-aspartyl-glutamate that is present in a biological sample when it is obtained from a subject. On the other hand, the term "exogenous NAAG" refers to N-acetyl-aspartyl-glutamate, or a N-acetyl-aspartyl-glutamate derivative that was not present in a biological sample when it is obtained from a subject. In certain embodiments, the exogenous NAAG contains a detectable marker, such a radioactive marker or a fluorophore.

The term "GCP inhibitor" or "agent that inhibits GCP" refers to an agent that decreases the ability of a GCP to cleave NAAG into N-acetyl-aspartate and glutamate and/or decreases the level of GCP protein. In some embodiments the GCP inhibitor has an $IC_{50}$ of less than 1 µM, 500 nM, 250 nM, 200 nM, 150 nM, 100 nM, 75 nM, 50 nM or 25 nM. In some embodiments, a GCP inhibitor may decrease the cellular level of a GCP protein by at least about 10%, 25%, 50%, 75%, 90% or 95%.

As used herein, the term "subject" refers to a mammal, e.g., a human, mouse, rat, guinea pig, dog, cat, horse, cow, pig, or non-human primate, such as a monkey, chimpanzee, baboon or rhesus. In some embodiments, the subject is a human.

Methods for Quantitating GCP Activity

In some embodiments, described herein are methods for quantitating GCP activity in a biological sample. In some embodiments, the methods include the steps of: reducing the amount of endogenous NAAG in the biological sample, contacting the biological sample with exogenous NAAG, incubating the sample for a period of time and under conditions that allow any GCP present in the sample to cleave at least some of the exogenous NAAG into NAAG cleavage products (e.g., glutamate and NAA), and detecting the amount of exogenous NAAG cleavage product in the biological sample. The level of exogenous NAAG cleavage product detected correlates with the level of GCP in the biological sample.

The methods described herein can be used to quantitate GCP activity in any biological sample that contains cells that expresses GCP, including samples that contain skin tissue, central nervous system tissue, peripheral nervous system tissue, intestinal tissue and prostate tissue. The methods described herein are particularly well suited for measuring GCP activity skin biopsy samples. Notably, previous attempts at quantitating GCP activity in skin biopsy samples have been unsuccessful.

In certain embodiments, the methods described herein include the step of reducing the amount of endogenous NAAG in the biological sample. Reduction of endogenous NAAG levels can be accomplished using any appropriate method known in the art. For example, because GCP is a membrane-bound protein while NAAG is a soluble dipeptide, any method for the isolation plasma membrane-bound material from soluble material can be used to reduce the levels of endogenous NAAG in the biological sample. For example, as described in the exemplification, the biological sample can be homogenized (e.g., using sonication) and then centrifuged under conditions wherein the GCP-containing plasma membranes are pelleted, while the cytosolic fraction remains in the supernatant (e.g., centrifuged for about 2 minutes at about 16,000×g), and the supernatant removed. Alternatively, commercially available kits for the isolation of plasma membrane proteins can be used, such as the Qproteome Plasma Membrane Protein Kit from Qiagen, or the Mem-PER Eukaryotic Membran Protein Extraction Kit from Thermo Scientific.

In some embodiments, the methods described herein include a step whereby the biological sample is contacted with exogenous NAAG and the level of GCP in the biological sample is determined through the detection of an exogenous NAAG cleavage products. As described above, GCP cleaves NAAG into glutamate and NAA. In certain embodiments, the exogenous NAAG includes a detectable label. In such embodiments, the exogenous NAAG cleavage products are detected through the detection of this detectable label. Any detectable label that does not interfere with GCP's ability to cleave NAAG can be used in the methods described herein, including radioactive labels, fluorescent labels, enzymatic labels, colorimetric labels and/or chemiluminescent labels. In some embodiments, the detectable label is a radioactive label. For example, in some embodiments the exogenous NAAG is [$^3$H]-NAAG. The detectable label can be incorporated into the exogenous NAAG such that either glutamate, NAA or both remain detectably labeled following NAAG cleavage by GCP.

In some embodiments, the detected exogenous NAAG cleavage product is separated from the remaining exogenous NAAG prior to detection. Separation of the exogenous NAAG cleavage product can be accomplished using any method known in the art, including, for example, using ion exchange chromatography, reverse phase high pressure liquid chromatography and gas chromatography. Thus, for example, exogenous detectably labeled exogenous NAAG can be separated from detectably labeled glutamate using strong cation exchange chromatography, as described in the exemplification provided herein below.

The methods used for the detection of the exogenous NAAG cleavage product will vary depending upon whether the exogenous NAAG is detectably labeled and, if it is labeled, what type of label is used. Methods useful for the detection of the NAAG cleavage products NAA and glutamate are well known in the art. For example, if the exogenous NAAG was not labeled, the NAAG cleavage products can be detected using HPLC or LC-MS/MS. On the other hand, if the exogenous NAAG incorporates a detectable label, any method known in the art for the detection of that detectable label can be used to detect the exogenous NAAG cleavage product. For example, if the exogenous NAAG is radioactively labeled, a scintillation counter can be used to detect the presence of the exogenous NAAG cleavage product, while if the exogenous NAAG incorporates a fluorescent label a fluorometer can be used to detect the presence of the exogenous NAAG cleavage product.

Methods for Determining Whether an Agent Inhibits GCP in a Subject

In some embodiments, provided herein are methods for determining whether an agent (or a particular dose of an agent) inhibits GCP activity in a subject. Such methods are useful, for example, when GCP activity is being used as a pharmacodynamic marker to determine what doses of the agent are required to elicit pharmacologic responses. Such methods are also useful, for example, for determining whether a patient has received an appropriate dose of a therapeutic GCP inhibiting agent.

In certain embodiments, the methods described herein include the steps of: administering an agent to a subject, obtaining a biological sample from the subject, reducing the amount of endogenous NAAG in the biological sample, contacting the biological sample with exogenous NAAG, incubating the sample for a period of time and under conditions that allow any GCP present in the sample to cleave at least some of the exogenous NAAG into NAAG cleavage products (e.g., glutamate and NAA), and detecting the amount of exogenous NAAG cleavage product in the biological sample. In general, the level of exogenous NAAG cleavage product in the biological sample correlates with the level of active GCP in the biological sample.

In some embodiments, the level of exogenous NAAG cleavage product in the biological sample is compared to the level of exogenous NAAG cleavage product in a control sample. The control sample can be any sample of the same tissue type and from the same species as the test biological sample, but that was obtained from a subject who did not receive the agent prior to sample collection. For example, in some embodiments, the control sample is obtained from the same subject as the test biological sample, but is obtained before the agent is administered to the subject. In some embodiments, the control sample is collected from a different subject, or it includes tissue collected from a plurality of subjects. In general, if the amount of NAAG cleavage product in the test biological sample is less than the amount of NAAG cleavage product in the control sample, the administered agent inhibits GCP in the subject at the dose that was administered.

The biological sample used in the methods described herein can contain any tissue that expresses GCP, including skin tissue, central nervous system tissue, peripheral nervous system tissue, intestinal tissue and/or prostate tissue. As described above, the methods described herein are particularly applicable to measuring GCP activity in skin biopsy samples. Because skin biopsies are relatively non-invasive, it is possible to obtain a series of skin biopsies at different times from the same patient without causing the patient unacceptable discomfort. The methods described herein therefore enable the tracking of the GCP inhibitory activity of an agent in a subject over time. Thus, in certain embodiments, the methods described herein are performed on a plurality of biological samples obtained from the same subject at different time points prior to and/or following administration of the agent.

In certain embodiments, the methods described herein include the step of reducing the amount of endogenous NAAG in the biological sample. Reduction of endogenous NAAG levels can be accomplished using any appropriate method known in the art. For example, because GCP is a membrane-bound protein while NAAG is a soluble dipeptide, any method for the isolation plasma membrane-bound material from soluble material can be used to reduce the levels of endogenous NAAG in the biological sample. For example, as described in the exemplification, the biological sample can be homogenized (e.g., using sonication) and then centrifuged under conditions wherein the GCP-containing plasma membranes are pelleted, while the cytosolic fraction remains in the supernatant (e.g., centrifuged for about 2 minutes at about 16,000×g), and the supernatant removed. Alternatively, commercially available kits for the isolation of plasma membrane proteins can be used, such as the Qproteome Plasma Membrane Protein Kit from Qiagen, or the Mem-PER Eukaryotic Membran Protein Extraction Kit from Thermo Scientific.

In some embodiments, the methods described herein include a step whereby the biological sample is contacted with exogenous NAAG and the level of GCP in the biological sample is determined through the detection of an exogenous NAAG cleavage products. As described above, GCP cleaves NAAG into glutamate and NAA. In certain embodiments, the exogenous NAAG includes a detectable label. In such embodiments, the exogenous NAAG cleavage products are detected through the detection of this detectable label. Any detectable label that does not interfere with GCP's ability to cleave NAAG can be used in the methods described herein, including radioactive labels, fluorescent labels, enzymatic labels, colorimetric labels and/or chemiluminescent labels. In some embodiments, the detectable label is a radioactive label. For example, in some embodiments the exogenous NAAG is [$^3$H]-NAAG. The detectable label can be incorporated into the exogenous NAAG such that either glutamate, NAA or both remain detectably labeled following NAAG cleavage by GCP.

In some embodiments, the detected exogenous NAAG cleavage product is separated from the remaining exogenous NAAG prior to detection. Separation of the exogenous NAAG cleavage product can be accomplished using any method known in the art, including, for example, using ion exchange chromatography, reverse phase high pressure liquid chromatography and gas chromatography. Thus, for example, exogenous detectably labeled exogenous NAAG can be separated from detectably labeled glutamate using strong cation exchange chromatography, as described in the exemplification provided herein below.

The methods used for the detection of the exogenous NAAG cleavage product will vary depending upon whether the exogenous NAAG is detectably labeled and, if it is labeled, what type of label is used. Methods useful for the detection of the NAAG cleavage products NAA and glutamate are well known in the art. For example, if the exogenous NAAG was not labeled, the NAAG cleavage products can be detected using HPLC or LC-MS/MS. On the other hand, if the exogenous NAAG incorporates a detectable label, any method known in the art for the detection of that detectable label can be used to detect the exogenous NAAG cleavage product. For example, if the exogenous NAAG is radioactively labeled, a scintillation counter can be used to detect the presence of the exogenous NAAG cleavage product, while if the exogenous NAAG incorporates a fluorescent label a fluorometer can be used to detect the presence of the exogenous NAAG cleavage product.

In certain embodiments, the methods described herein include the administration of an agent, such as an agent that inhibits GCP. Exemplary agents that inhibit GCP include, for example, small molecules, inhibitory nucleic acids (e.g., siRNA or shRNA molecules specific for GCP mRNA), antibodies (e.g., antibodies that bind to GCP protein) and polypeptides (e.g., polypeptides that bind to the biologically active portion of the GCP protein). Exemplary GCP inhibitors are described in, for example, U.S. Pat. Nos. 5,880,112; 5,968,915; 6,025,344; 6,384,022; 6,348,464; 7,148,250 and U.S. Patent Pub. Nos. 2006/0135812; 2005/0080139, each of which is incorporated by reference in its entirety.

Agents useful in the methods described herein may be obtained from any available source, including systematic libraries of natural and/or synthetic compounds. Agents may also be obtained by any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al., 1994, *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of agents may be presented in solution (e.g., Houghten, 1992, *Biotechniques* 13:412-421), or on beads (Lam, 1991, *Nature* 354:82-84), chips (Fodor, 1993, *Nature* 364:555-556), bacteria and/or spores, (Ladner, U.S. Pat. No. 5,223,409), plasmids (Cull et al, 1992, *Proc Natl Acad Sci USA* 89:1865-1869) or on phage (Scott and Smith, 1990, *Science* 249:386-390; Devlin, 1990, *Science* 249:404-406; Cwirla et al, 1990, *Proc. Natl. Acad. Sci.* 87:6378-6382; Felici, 1991, *J. Mol. Biol.* 222:301-310; Ladner, supra.).

Agents useful in the methods described herein may be identified, for example, using assays for screening candidate or test agents which inhibit the activity of GCP. For example, candidate or test agents can be screened for the ability to inhibit the cleavage of NAAG by GCP.

The basic principle of the assay systems used to identify agents that inhibit the activity of GCP involves preparing a reaction mixture containing GCP and NAAG under conditions and for a time sufficient to allow GCP to cleave NAAG into NAA and glutamate. In order to test an agent for modulatory activity, the reaction mixture is prepared in the presence and absence of the test agent. The test agent can be initially included in the reaction mixture, or can be added at a time subsequent to the addition of GCP and NAAG. Control reaction mixtures are incubated without the test agent or with a placebo. The cleavage of NAAG by GCP is then detected using standard methodologies. For example, disappearance of NAAG and/or the formation of NAA or glutamate can be measured in the sample using mass spectrometry or liquid chromatography. The cleavage activity in the control reaction, but less or no such cleavage in the reaction mixture containing the test agent, indicates that the agent inhibits the activity of GCP.

Modulators of GCP expression may also be identified, for example, using methods wherein a cell that expresses GCP is contacted with a candidate agent and the expression of GCP mRNA or protein is determined using standard methods known in the art. The level of expression of mRNA or protein in the presence of the candidate agent is compared to the level of expression of mRNA or protein in the absence of the candidate agent. The candidate agent can then be identified as an inhibitor of GCP expression based on this comparison.

EXAMPLES

Example 1

GCP Activity is Present in Human Skin Biopsies

Punch skin biopsies (3 mm) were obtained from the distal thigh of healthy human volunteers after anesthesia with 0.5 cc 2% lidocaine subcutaneous injection. Samples were placed in cold Tris buffer (pH 7.4) and GCP enzymatic activity was carried out within 1 hour of collection. The skin were homogenized, the homogenate was centrifuged and the pellet was used as source of GCP in the enzyme activity assay. Briefly, human skin biopsies were sonicated in Tris buffer (pH 7.4, 40 mM, 0.5 mL) for 1 minute in ice. The mixture was centrifuged for 2 minutes at 16000×g; the supernantant (containing endogenous NAAD) was removed and the resulting pellet (containing GCP) was reconstituted in 70 μL assay buffer (Tris pH 7.4, 40 mM containing 1 mM $CoCl_2$) and used as source of GCP in the activity assay. Reconstituted pellet was then incubated with [$^3$H] NAAG and production of glutamate was determined in the presence and absence of 2-PMPA, a highly selective GCP inhibitor. Briefly, the reaction mixture containing [$^3$H]-NAAG (70 nM, 50 Ci/mmol) and reconstituted pellet in Tris-HCl containing 1 mM $CoCl_2$ in a total volume of 90 μL was incubated at 37° C. for different lengths of time in the presence and absence of the selective GCP inhibitor 2-PMPA (1 μM). Negative controls were obtained by incubating the reaction mixture without pellet. Reactions were stopped with ice-cold sodium phosphate buffer (pH 7.4, 0.1 M, 90 μL). Duplicate aliquots of 90 μL from each terminated reaction was transferred to a well in a 96-well spin column containing AG1X8 ion-exchange resin; the plate was centrifuged at 1000 rpm for 5 minutes using a Beckman GS-6R centrifuge equipped with a PTS-2000 rotor. [$^3$H]-NAAG bound to the resin and [$^3$H]-glutamate eluted in the flow through. Columns were then washed twice with formate (1 M, 90 μL) to ensure complete elution of [$^3$H]-glutamate. The flow through and the washes were collected in a deep 96-well block; from each well with a total volume of 270 μL, a 200 μL aliquot was transferred to a glass scintillation vial, to which 10 ml of Ultima-Gold (Perkin Elmer) was added. The radioactivity in each vial corresponding to [$^3$H]-glutamate was determined via a Beckman LS-6000IC scintillation counter. Radioactivity values in dpm were converted to fmoles of glutamate using the relation 1 pCi/2.2 dpm and the specific activity of [$^3$H]-glutamate (same as that of [$^3$H]-NAAG: 1 fmole/50 pCi). As a result, if 16711 dpm [$^3$H]-glutamate were measured after incubating 10 mg tissue for 1 h, the normalized activity would be: 16711 dpm×(1 pCi/2.2 dpm)×(1 fmole/50 pCi)/10 mg tissue=15 fmole/h/mg tissue.

When pellets obtained from human skin biopsy were used, conversion to glutamate was 11±0.2 fmole glutamate generated/h/mg tissue.

When whole homogenate preparations of human skin were tested without removing endogenous NAAG, the samples exhibited a very low GCP activity that was difficult to measure. However, when endogenous NAAG was removed by centrifugation and isolation of the resulting pellet, (using the sample preparation method described herein above), the pellet preparations exhibited measurable GCP activity that was inhibited by 90% when 2-PMPA, a highly specific GCP inhibitor, was added to the assay mixture.

Figure 1:
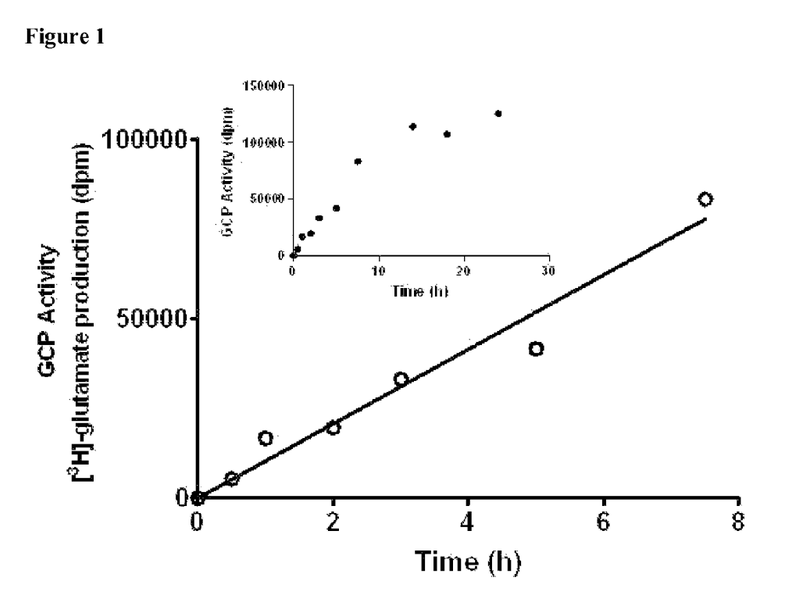

A time course of glutamate production after different incubation times (0.5, 1, 2, 3, 5, 7.5, 14, 18 and 24 h) was carried out. GCP activity was linear for the first 7.5 h of incubation (FIG. 1). [$^3$H]-NAAG at 70 nM (~770,000 dpm) provided robust sensitivity to follow GCP activity; there were approximately 5,000 and 80,000 dpm of [$^3$H]-glutamate after 0.5 and 7.5 h incubation respectively. These values corresponded to 0.6 and 10% conversion of reactant to product indicating that sufficient substrate concentration was used and that if additional GCP activity had been present, additional activity would have been observed.

Example 2

Peripheral Administration of 2-PMPA Inhibits GCP Activity in Skin and Sciatic Nerve Samples A determination of GCP activity was carried out using male Wistar rat paw pads. Skin was collected from the planter hindpaw by 3 mm skin biopsy dissection and sonicated for 2 minutes in ice. The mixture was centrifuged for 2 minutes at 16000×g and the resulting pellet was reconstituted similar to the pellets obtained from the human skin dissections. Reconstituted pellet preparations from rat paw pads were used as source of GCP II and incubated with [$^3$H] NAAG, as described above for the human skin samples. The amount of GCP activity in rat paw pads was found to be 15±0.2 fmole glutamate generated/h/mg tissue. The amount of GCP activity found in rat paw pads (15±0.2 fmole/h/mg tissue) was similar to that obtained from human skin (11±0.2 fmole/h/mg tissue).

Figure 2:
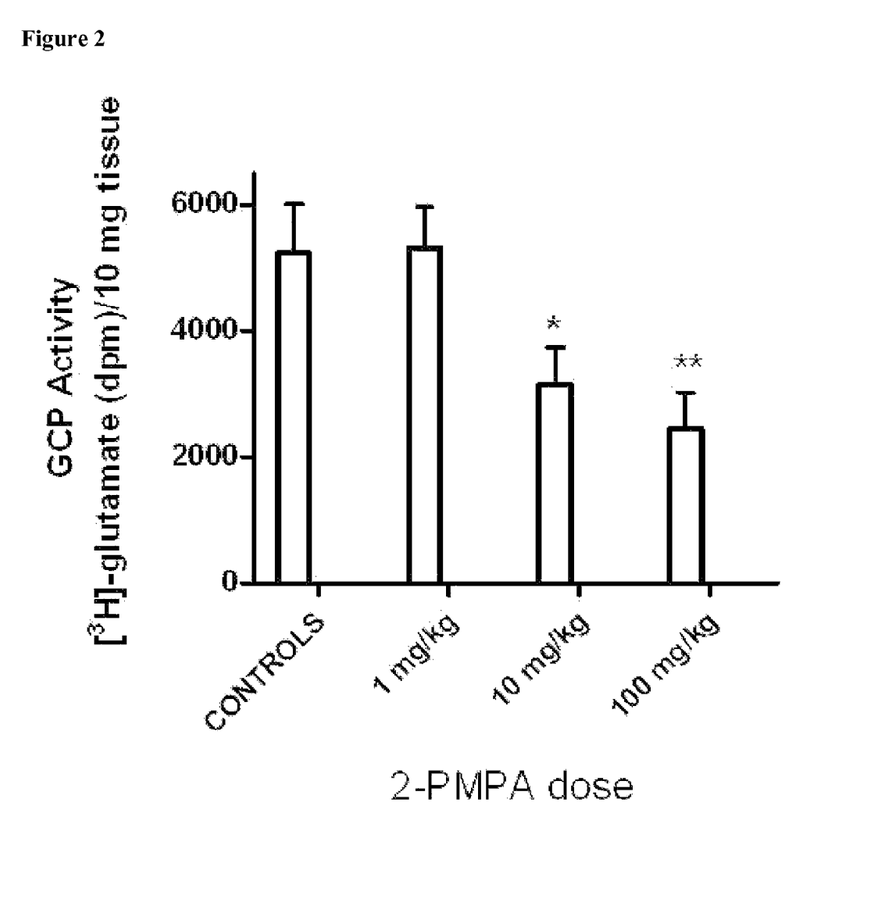
FIG. 2 shows that GCP activity in rat paw pads is inhibited by peripheral administration of 2-PMPA. Rats were treated with 2-PMPA (1, 10 and 100 mg/kg i.p.) as well as vehicle control. Animals were sacrificed 1 hour after compound administration, paw pads isolated and GCP activity determined.

In order to determine if GCP activity in skin in vivo could be inhibited by peripheral administration of 2-PMPA, rats were administered vehicle (HEPES saline, pH 7, 50 mM) or 2-PMPA (1, 10 and 100 mg/kg, i.p.) using a dosing volume of 2 mL/kg. There were 10 animals in each group. Animals were sacrificed 1 hour after 2-PMPA or vehicle administration. Animals were sacrificed 1 hour after compound administration, paw pads isolated and GCP activity determined as described herein above. GCP activity in paw pad preparations from animals treated with 1 mg/kg 2-PMPA was similar to that of controls. On the other hand, paw pads from animals treated with 10 and 100 mg/kg exhibited significantly reduced GCP activity: 60±11 and 47±11% respectively when compared to control animals (FIG. 2). These are the doses of 2-PMPA previously shown to exhibit therapeutic benefit.

Figure 3:
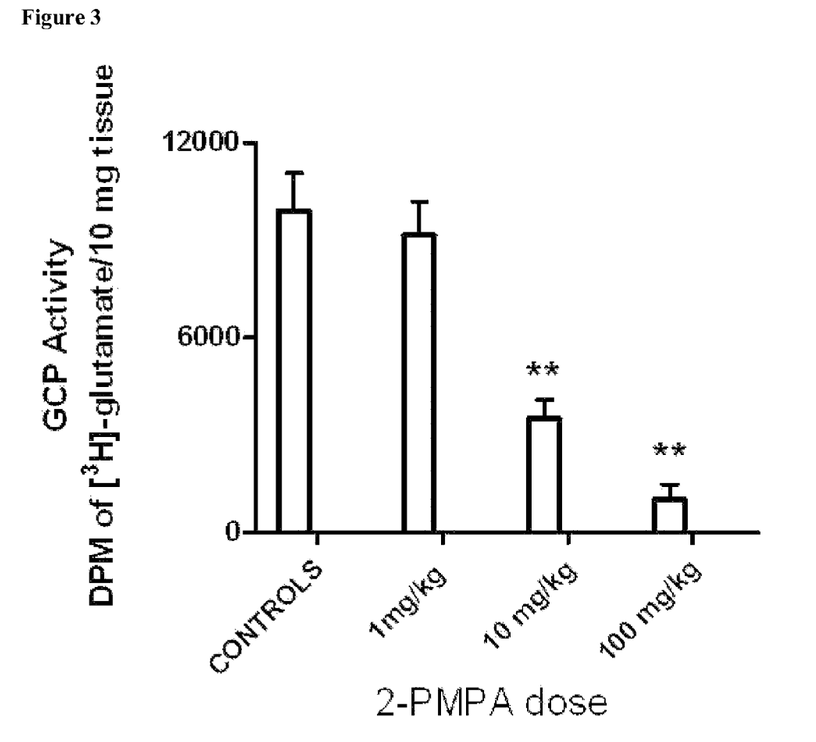
FIG. 3 shows GCP activity in rat sciatic nerve is inhibited by peripheral administration of 2-PMPA. Rats were treated with 2-PMPA (1, 10 and 100 mg/kg i.p.) as well as vehicle control. Animals were sacrificed 1 hour after compound administration, sciatic nerve isolated and GCP activity determined.

Sciatic nerve is the target tissue for GCP inhibitors in clinical trials for peripheral neuropathy and neuropathic pain. To obtain sciatic nerve samples, 1-2 cm incisions were made to the skin on top of the rat's mid-thigh so that sciatic nerve, gluteus superficialis muscle and biceps femoris muscle were exposed. The three were then separated and 5 mm of sciatic nerve was removed and analyzed as described above for the human skin and rat paw pad samples. GCP activity in sciatic nerve preparations from animals treated with 1, 10 and 100 mg/kg 2-PMPA was reduced to 92±11, 35±6 and 10±4% respectively compared to activity in sciatic nerve isolated from control animals (FIG. 3). Albeit to a different extent, GCP inhibition in sciatic nerve is attained at similar 2-PMPA doses (10 and 100 mg/kg i.p.) as in footpad tissue. Taken together, these results indicate that GCP inhibition in the skin can be followed as a marker of GCP inhibition in peripheral nerve.

The presence of 2-PMPA in skin was determined. Animals were given 2-PMPA (100 mg/kg, i.p.), sacrificed 1 hour after compound administration and paw pads isolated for direct determination of 2-PMPA levels by LC-MS/MS. Since 2-PMPA detection by mass spectrometry has low sensitivity due to ion suppression, samples from animals that had received 100 mg/kg 2-PMPA rather than 10 mg/kg were analyzed to increase the probability of detecting 2-PMPA.

Briefly, frozen samples were thawed in a water bath at ambient temperature and subjected to a liquid extraction using MeOH. Samples were placed in brown glass vials containing 500 μL of 100% MeOH. The vial was capped and mixed vigorously for 10 seconds on a vortex-mixer followed by 30 minutes on an automated multitude shaker, followed by incubation for 24 hours at 4° C. The top organic layer was transferred to a disposable borosilicate glass culture tube (13×100 mm) and evaporated to dryness at 40° C. under a gentle stream of nitrogen. The residue was reconstituted in 100 μL acetonitrile-water (1:1, v/v) containing the internal standard, temazepam (50 μg/mL), by vortex mixing (30 sec) and immersion in an ultrasound bath (5 min). The sample was transferred to a 250 μL polypropylene auto sampler vial sealed with a Teflon crimp cap, and a volume of 50 μL was injected onto the HPLC instrument for quantitative analysis using a temperature-controlled auto sampling device operating at 10° C.

Chromatographic analysis was performed using a Waters ACQUITY UPLC (Milford, Mass., USA). Separation of the analytes from potentially interfering material was achieved at ambient temperature using a Waters Altantis column (100× 2.1 mm i.d.) packed with a 3 μm ODS stationary phase, protected by a guard column packed with 3.5 μm RP18 material (Milford, Mass., USA). The mobile phase used for the chromatographic separation was composed of acetonitrile-water (60:40, v/v) containing 0.1% formic acid, and was delivered isocratically at a flow rate of 0.3 mL/min. The column effluent was monitored using an AB SCIEX TRIPLE QUAD 5500 triple-quadrupole mass-spectrometric detector (Applied Biosystems, Foster City, Calif., USA). The instrument was equipped with an electrospray interface, operated in a positive mode and controlled by the Analyst version 1.5 software (Applied Biosystems). The spectrometer was programmed to allow the [MH+] ion of 2-PMPA at m/z 226.8 and that of the internal standard at m/z 301.1 pass through the first quadrupole (Q1) and into the collision cell (Q2). The daughter ions for 2-PMPA (m/z 191.1) and the internal standard (m/z 255.1) were monitored through the third quadrupole (Q3). Calibration curves were generated over the range of 200 to 10,000 ng/mL. Mouse paw pad samples were then quantitated in μg/g as: nominal concentration (ng/mL)×0.0625 (standardized dilution)×sample weight (in mg).

Figure 4:
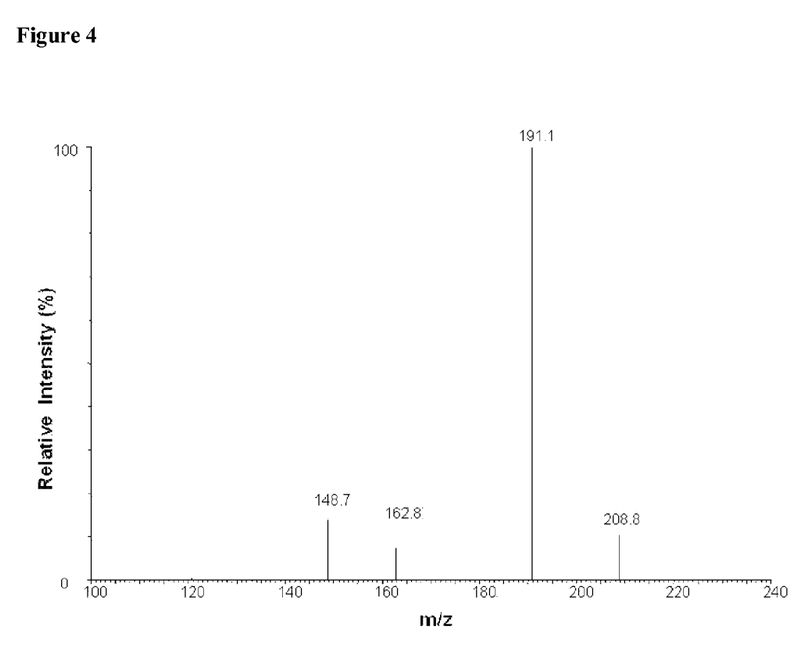
FIG. 4 shows a daughter-scan product ion spectrum of 2-PMPA, as determined using LC-MS/MS. Monitoring was carried out at m/z 226.8→191.1.
Figure 5:
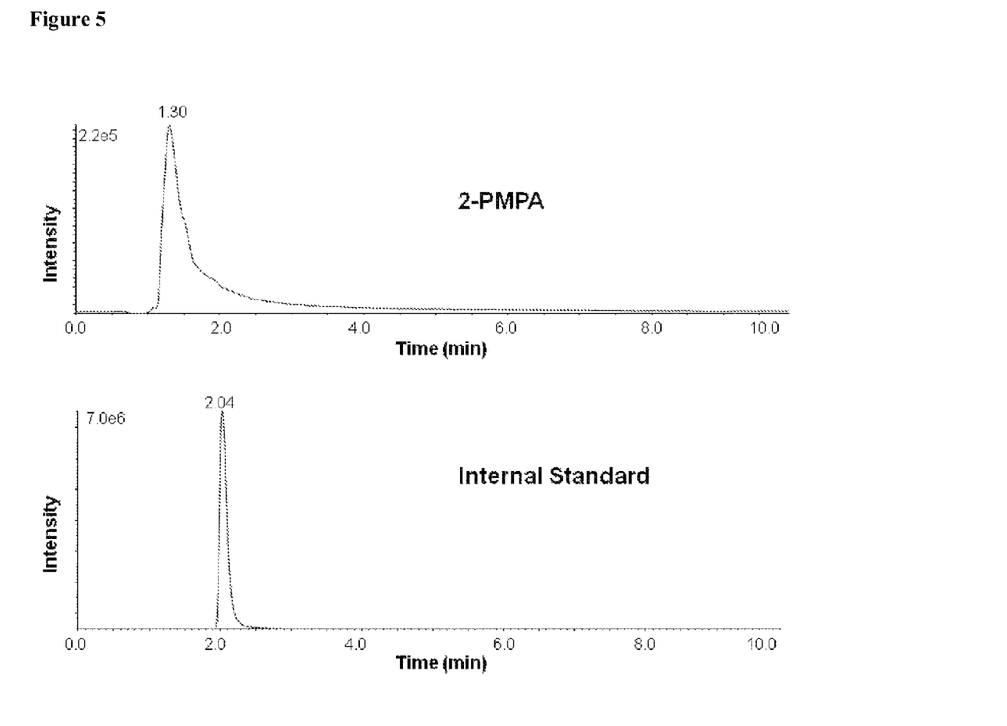
FIG. 5 shows the retention times for 2-PMPA and internal standard (temazepan) (approximately 1.3 and 2.0 min respectively) as determined using LC-MS/MS to analyze paw pad samples from rats treated with 2-PMPA. When rodent paw pads from untreated animals were used, only the internal standard peak was observed.

The characteristic fragmentation pattern for 2-PMPA was readily detected (FIG. 4) and the chromatographic peaks of 2-PMPA and internal standard (FIG. 5) allowed for quantitation of material in the sample. Paw pads from animals that were treated with compound showed 38±5 μg/g tissue (n=9) (FIG. 5) a concentration high enough to inhibit GCP activity, while the compound was undetectable in paw pads isolated from vehicle-treated animals.

We claim:

1. A method of quantitating glutamate carboxypeptidase II (GCPII) activity in a biological skin sample that contains endogenous N-acetyl-aspartate glutamate (NAAG), the method comprising the steps of:
   (a) reducing the amount of the endogenous NAAG in a biological skin sample;
   (b) contacting the biological skin sample with exogenous NAAG; and
   (c) detecting an exogenous NAAG cleavage product in the biological skin sample.

2. The method of claim 1, wherein the biological skin sample is a skin biopsy collected from a subject.

3. The method of claim 2, wherein the subject had been administered a GCPII inhibitor before the skin biopsy was collected.

4. The method of claim 1, wherein the step of reducing the amount of endogenous NAAG in the biological skin sample comprises the steps of:
   (i) homogenizing the biological sample in a buffer to create a homogenate;
   (ii) centrifuging the homogenate to create a sample pellet that contains the GCPII and a supernatant that contains the endogenous NAAG; and
   (iii) removing the supernatant from the sample.

5. The method of claim 4, wherein the sonication is used to homogenize the biological skin sample.

6. The method of claim 1, wherein the exogenous NAAG comprises a detectable label that is detected in step (c) as an indication of the presence of the exogenous NAAG cleavage product.

7. The method of claim 6, wherein the detectable label is a radioactive, fluorescent, enzymatic, colorimetric or chemiluminescent label.

8. The method of claim 1, wherein the exogenous NAAG cleavage product is glutamate or N-acetyl-aspartate (NAA).

9. The method of claim 1, wherein the exogenous NAAG cleavage product is separated from remaining exogenous NAAG before step (c).

10. The method of claim 9, wherein the exogenous NAAG cleavage product is separated from the remaining exogenous NAAG using strong cation exchange.

11. A method of determining whether an agent is inhibiting GCPII in a subject, the method comprising the steps of:
   (a) administering the agent to the subject;
   (b) obtaining a biological skin sample from the subject;
   (c) reducing the amount of endogenous NAAG in the biological skin sample;
   (d) contacting the biological skin sample with exogenous NAAG; and
   (e) detecting the amount of an exogenous NAAG cleavage product in the biological skin sample;
wherein a lower amount of the exogenous NAAG cleavage product in the biological skin sample compared to the amount of exogenous NAAG cleavage product in a control skin sample indicates that the agent is inhibiting GCPII in the subject.

12. The method of claim 11, wherein the control skin sample is a sample that was obtained from the subject before the agent was administered to the subject.

13. The method of claim 11, wherein the biological skin sample and the control sample are each skin biopsies obtained from the subject.

14. The method of claim 11, wherein the step of reducing the amount of endogenous NAAG in the biological skin sample comprises the steps of:

(i) homogenizing the biological skin sample in a buffer to create a homogenate;
(ii) centrifuging the homogenate to create a sample pellet that contains GCPII and a supernatant that contains endogenous NAAG; and
(iii) removing the supernatant from the sample.

15. The method of claim 14, wherein the sonication is used to homogenize the biological skin sample.

16. The method of claim 11, wherein the exogenous NAAG comprises a detectable label that is detected in step (e) as an indication of the presence of the exogenous NAAG cleavage product.

17. The method of claim 16, wherein the detectable label is a radioactive, fluorescent, enzymatic, colorimetric or chemiluminescent label.

18. The method of claim 11, wherein the exogenous NAAG cleavage product is glutamate or N-acetyl-aspartate (NAA).

19. The method of claim 11, wherein the exogenous NAAG cleavage product is separated from remaining exogenous NAAG before step (c).

20. The method of claim 19, wherein the exogenous NAAG cleavage product is separated from the remaining exogenous NAAG using strong cation exchange.

* * * * *